United States Patent [19]
Karger et al.

[11] Patent Number: 5,122,248
[45] Date of Patent: Jun. 16, 1992

[54] PULSED FIELD CAPILLARY ELECTROPHORESIS

[75] Inventors: Barry L. Karger, Newton; Aharon S. Cohen, Brookline; David N. Heiger, Medford, all of Mass.

[73] Assignee: Northeastern University, Boston, Mass.

[21] Appl. No.: 525,532

[22] Filed: May 18, 1990

[51] Int. Cl.$^5$ .................. C25B 1/00; C25B 7/00; B01D 61/42
[52] U.S. Cl. ............... 204/182.8; 204/299 R; 204/180.1
[58] Field of Search ............ 204/299 R, 183.3, 182.8

[56] References Cited

U.S. PATENT DOCUMENTS

| | | | |
|---|---|---|---|
| 4,865,706 | 9/1989 | Karger | 204/182.8 |
| 4,909,919 | 3/1990 | Morris | 204/299 R |
| 4,911,807 | 3/1990 | Burd | 204/180.1 |
| 4,985,128 | 1/1991 | Ebersole | 204/182.8 |
| 5,015,350 | 5/1991 | Wiktorowicz | 204/180.1 |

OTHER PUBLICATIONS

Avdalovic, N. and Furst, A.: "An instrument for separating fragments of chromosomal DNA", American Biotech Laboratory, 26–34, May (1989).
Cantor, C., Smith, C. and Mathew, M.: "Pulsed-field gel Electrophoresis of very large DNA molecules", Ann. Rev. Biophys. Biophys. Chem. 17: 287 (1988).
Dawkins, H. J. S.: "Large DNA separation using field alternation agar gel electrophoresis", Journal of Chromatography, 492 (1989) 615–639, Elsevier Science Publishers B.V., Amsterdam.

Primary Examiner—John Niebling
Assistant Examiner—Caroline Koestner
Attorney, Agent, or Firm—Weingarten, Schurgin, Gagnebin & Hayes

[57] ABSTRACT

Apparatus and method for conducting electrophoresis in a capillary tube under the influence of a pulsed electric field. Apparatus for separating and detecting molecular species of a sample in a conductive medium includes a capillary tube for containing conductive medium, means for introducing a sample into a conductive medium-filled capillary tube, means for applying a pulsed electric field across the conductive medium-filled capillary tube between its ends, and means for detecting constituent molecular species of a sample in a conductive medium-filled capillary tube as they traverse the tube. A method for separating and detecting molecular species of a sample in a conductive medium includes the steps of introducing the sample into a capillary tube filled with conductive medium, applying a pulsed electric field of up to 500 volts/centimeter between the ends of the capillary, and detecting the constituent molecular species of the sample as they traverse the capillary.

22 Claims, 8 Drawing Sheets

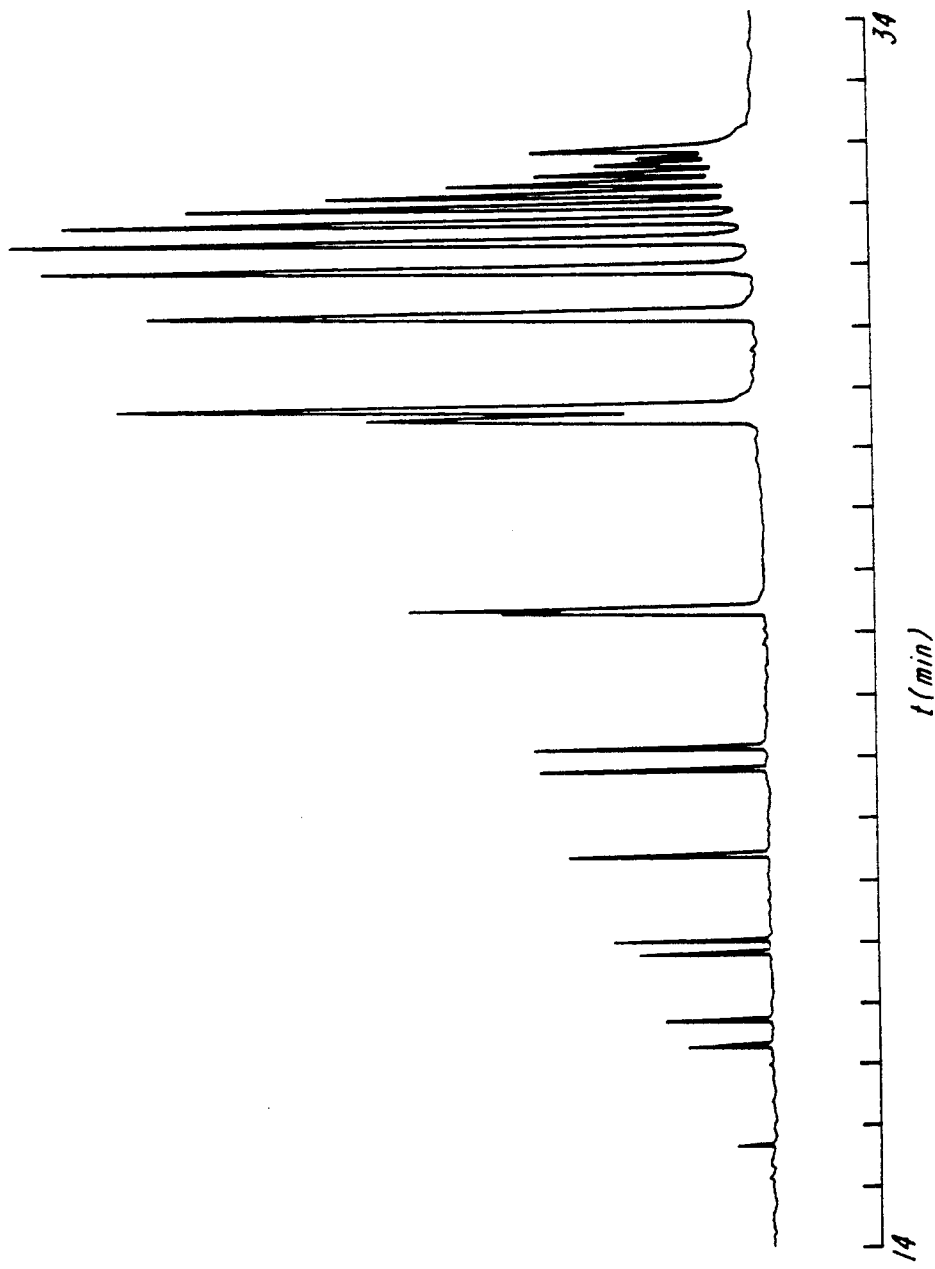

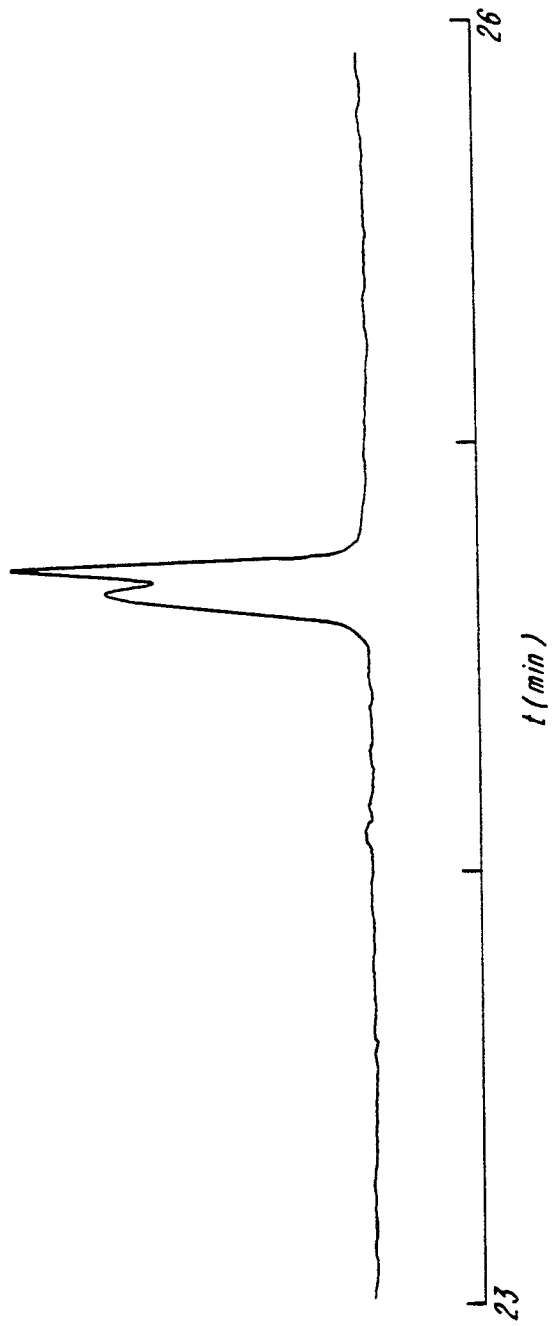

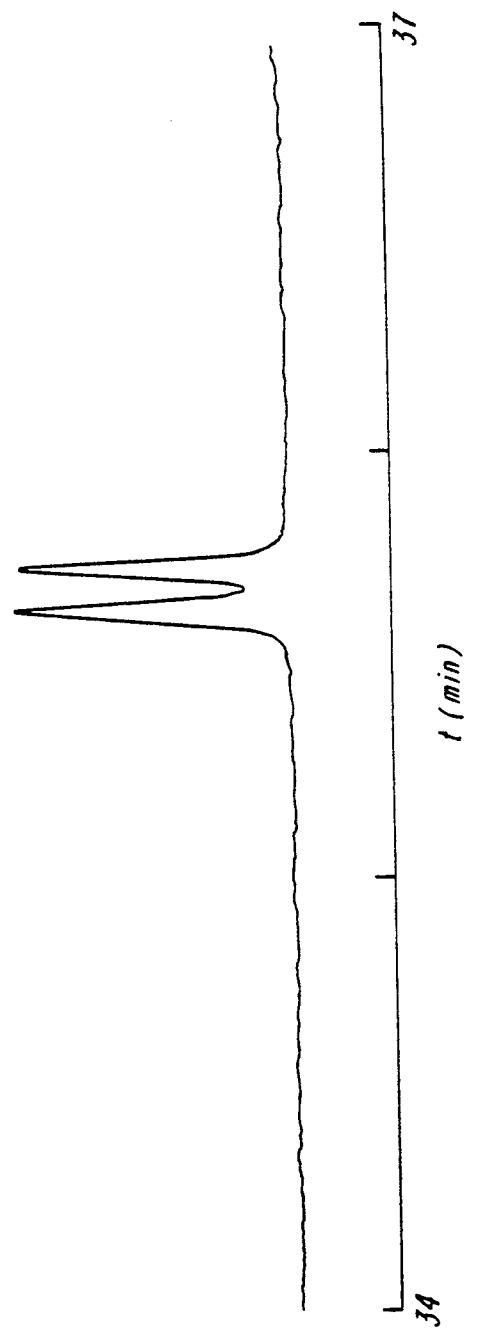

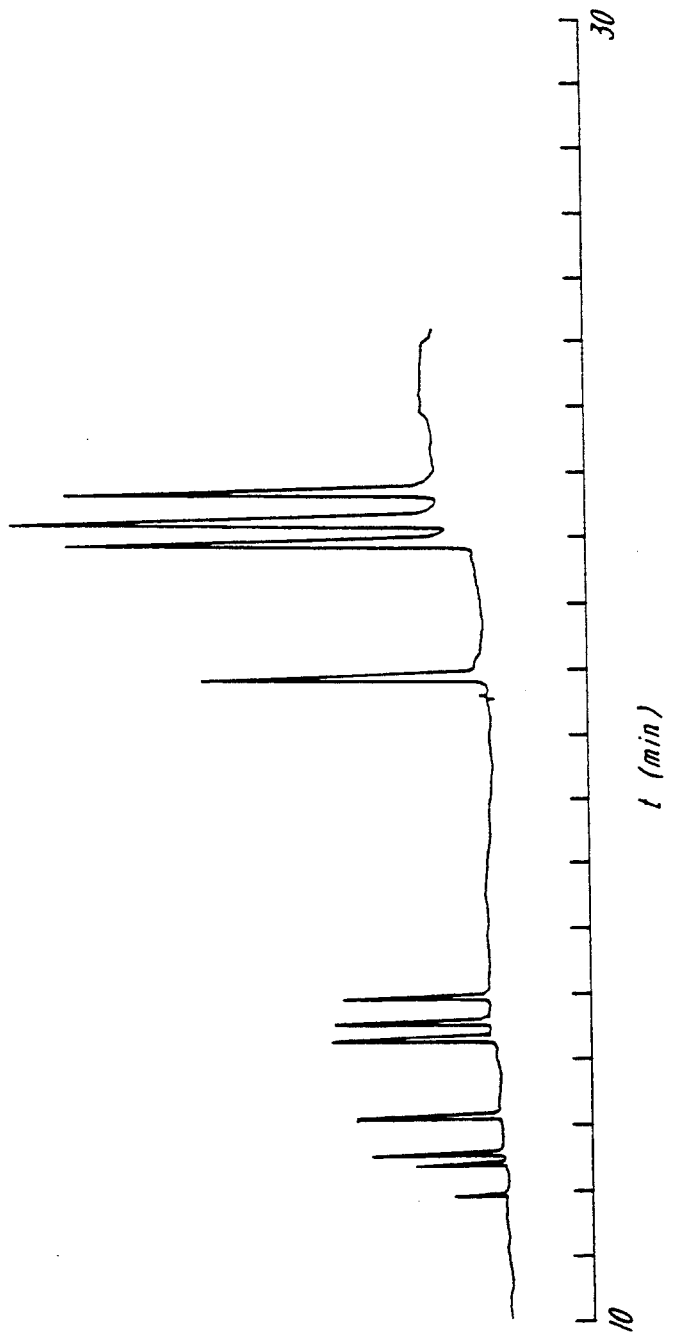

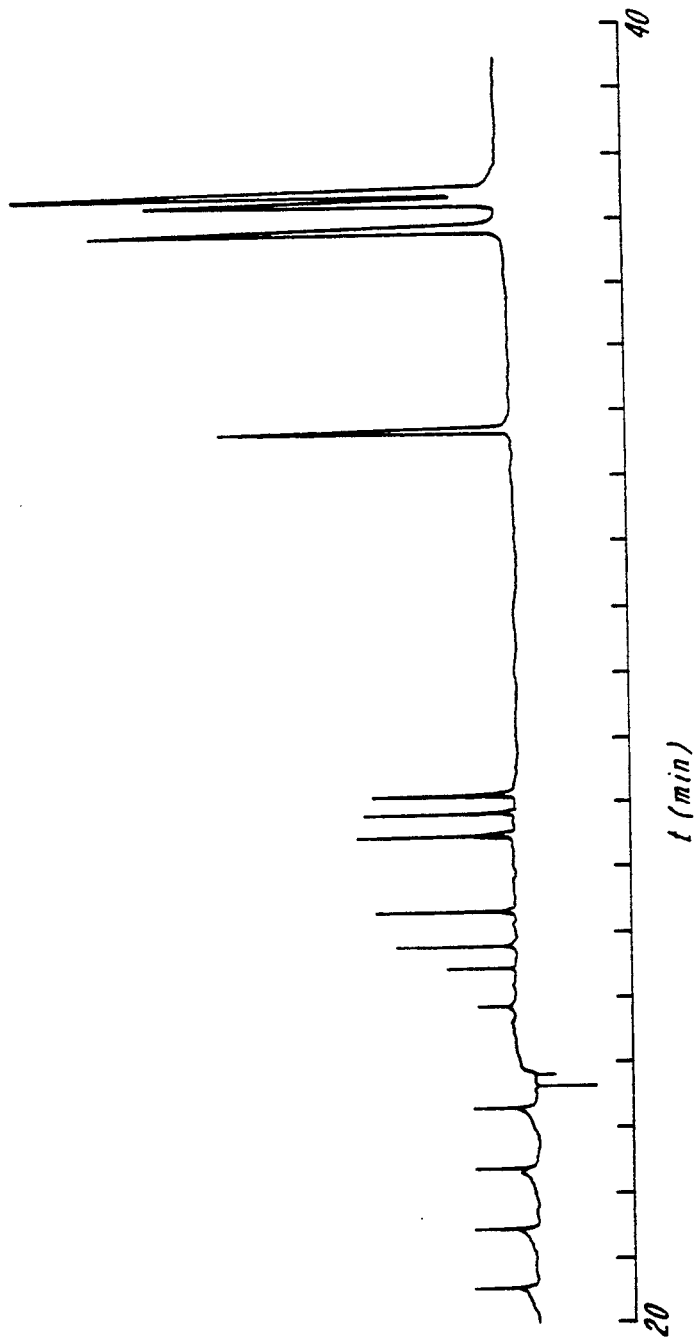

PULSED FIELD CAPILLARY ELECTROPHORESIS

FIELD OF THE INVENTION

This invention relates to electrophoresis, and more particularly, to pulsed field capillary electrophoresis.

BACKGROUND OF THE INVENTION

Pulsed field electrophoresis as practiced today for separations of high molecular weight biomolecules such as DNA is allow electric field technique. Flat slab gels are employed, with fields typically in the range of 10 volts per centimeter or less, with corresponding electric field amplitudes of 10 volts per centimeter or less. Separations require times ranging from hours to days.

Workers in the area of pulsed field electrophoretic separations of high molecular weight biomolecules such as DNA have determined experimentally that electric fields higher than about 10 volts per centimeter of the gel used for the electrophoresis degrade resolution, relative to the resolutions attainable employing pulsed fields of 10 volts per centimeter or less.

It has been postulated that this is caused by elongation of the molecules in strong fields, and alignment of the molecules with such fields, with the result that the molecules traverse the gel more or less "end-on" in a process called "reptaton." When the separating molecules are in this stretched out orientation, they presumably interact with pores of a given size in approximately the same manner regardless of their lengths, and so long as the molecular charge and the friction on the molecules are proportional to the molecular size, as is the case for DNA, the molecules tend to traverse the gel under given conditions at approximately the same velocities, resulting in poor separations. It has been expressly recognized in the literature, however, that the factors affecting resolution in these systems are not fully understood at present.

An electrophoretic technique which overcomes the deficiencies of pulsed field electrophoresis as presently practiced and provides good resolution of high molecular weight biomolecules such as DNA in relatively short separation times would be very useful in medical and biological/biochemical research and testing. Such a technique is the subject of the present invention.

SUMMARY OF THE INVENTION

Pulsed filed electrophoresis in capillaries can employ fields of up to 500 volts per centimeter successfully for separations of high molecular weight molecules such as DNA, with improved separation times relative to those of the prior art, on the order of minutes instead of hours or days. In addition, electrophoretic matrix compositions less viscous than prior art compositions used in slab gel electrophoresis may be employed, and for a given matrix provide the ability to perform separations on higher molecular weight materials than would be possible with more viscous compositions of that matrix.

According to the invention, apparatus for separating and detecting molecular species of a sample in a conductive medium includes: a capillary tube for containing a conductive medium, this tube having a cross sectional dimension of not more than 500 micrometers; means for introducing a sample into a conductive medium-filled capillary tube; means for applying a pulsed electric field across a conductive medium-filled capillary tube, between its ends, this pulsed electric field being effective to cause the constituent molecular species of the sample in the capillary tube to separate and traverse the tube; and means for detecting constituent molecular species of a sample in a conductive medium-filled capillary tube as they traverse this tube.

Further according to the invention, a method for separating and detecting molecular species of a sample in conductive medium includes the steps of: introducing the sample into a capillary tube having a cross sectional dimension of not more than 500 micrometers, this tube being filled with conductive medium; applying a pulsed electric field of up to 500 volts per centimeter of the capillary tube across this capillary tube, between its ends, the pulsed electric field being effective to cause the constituent molecular species of the sample in the tube to separate and traverse the tube; and detecting the constituent molecular species of the sample as they traverse the capillary tube.

DESCRIPTION OF THE DRAWING

The invention will be more completely understood from a consideration of the following detailed description taken in conjunction with the drawing, in which:

FIG. 5a is an electropherogram showing separation of a 1 kb ladder of DNA molecules from 75 bp to 12,000 bp, on a 4% T, 0% C polyacrylamide gel, under a continuous field of 250 volts per centimeter;

FIG. 5c is a time-expanded printout of the separation of the 23-26 minute portion of the electrophoresis run of FIG. 5a;

FIG. 5d is a time-expanded printout of the separation of the 34-37 minute portion of the electrophoresis run of FIG. 5b;

FIG. 6a is an electropherogram showing the separation of DNA molecules produced by Hae II digestion of φX174, on a 9% T, 0% C polyacrylamide capillary, under a continuous field of 285 volts per centimeter; and FIG. 6b is an electropherogram showing the separation of the DNA mixture of FIG. 5a on the same column, but with field pulsing being employed at the start of the run.

DETAILED DESCRIPTION

Figure 1:
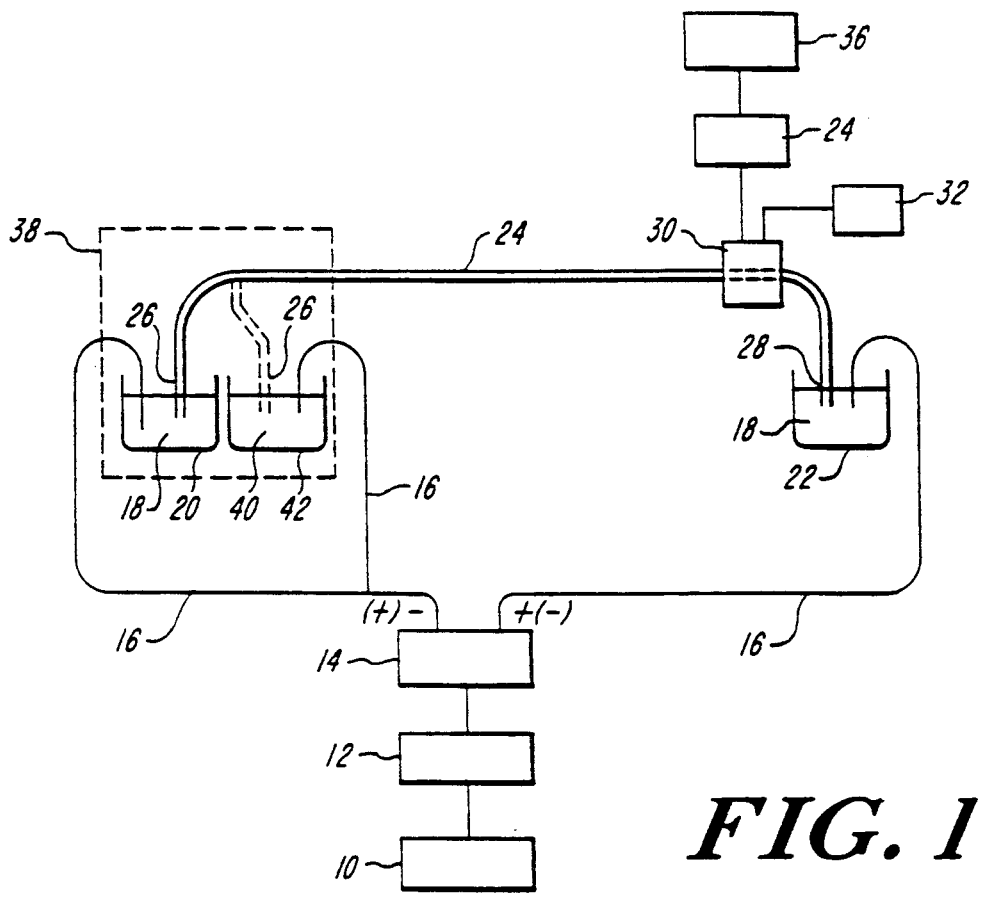
FIG. 1 is a schematic of apparatus for practicing pulsed field capillary electrophoresis.

FIG. 1 shows apparatus for conducting pulsed field capillary electrophoresis. A programmable computer 10 has its communication port connected to the input of a waveform generator 12, the output of which is in turn connected to the input of an amplifier 14. The output terminals of amplifier 14 are electrically connected via wires 16 to conducting medium 18 in containers 20 and 22. A capillary tube 24 filled with a conductive medium has its front end 26 immersed in conductive medium 18 in container 20. The rear end 28 of capillary tube 24 is immersed in conducting medium 18 in container 22. A detector 30 is located near rear end 28 of capillary tube 24 and communicates with capillary tuber 24. The output of detector 30 is connected to are recorder 32 and-/or to an A/D converter 34 which is in turn connected to computer 36. Computers 10 and 36 may be discrete deices or may be a single device. An optional automatic sample handler indicated schismatically as dashed box 38 in FIG. 1 is located near front end 26 of capillary tube 24, and contacts front end 26, container 20, or both. When optional automatic sampler 38 is employed, it will generally be electrically connected with computer 10.

Programmable computer 10 has the capacity to be programed, to direct waveform generator 12 to produce the field shapes, amplitudes, and frequencies desired to be employed in a given electrophoresis experiment. Where an automatic sample handler 38 is employed, programmable computer 10 also has the capacity to direct its operations. As computer control of the electrophoresis apparatus is not necessary for practicing the invention, programmable computer 10 is optional.

Waveform generator 12 may be an of a number of waveform generators, an example of one such device being Model 75 available from Wavetech of San Diego, Calif. Waveform generator 12 has a communication port through which its output can be transmitted to another device such as an amplifier. It is preferably capable of providing a wide variety of waveforms, including sine waves, square waves, triangular waves, positive and negative ramps, step functions, and other forms, and combinations thereof, in a positive or negative sense relative to a defined reference voltage. It will additionally provide for variable frequency and amplitude. An oscilloscope is generally employed in conjunction with the waveform generator so that the waveforms being employed may be viewed. Waveform generator may be run via computer control, or in stand-alone mode.

Amplifier 14 is preferably an operational amplifier capable of receiving the output waveforms from waveform generator 12 and amplifying the input signal to levels suitable for employment in the electrophoresis. A preferred amplifier is the Model PO 434 available from the Trek Corporation of Medina, N.Y. The amplifier preferably should be capable of providing an output electric field amplitude of up to 500 volts per centimeter of the capillary to be employed in the electrophoresis, of either positive or negative polarity.

Wires 16 may themselves make electrical contact with conducting medium 18, or may terminate in electrodes which make such contact.

Capillary tube 24 is filled with a conductive medium or matrix, typically a buffer solution, and will also usually include a sieving matrix, which may or may not be crosslinked. The capillary preferably has a diameter in the range 5-200 micrometers, capillaries having diameters in the range 50 to 100 micrometers being most preferred. Capillaries capable of operating under fields of several hundred volts per centimeter and in some cases as high as 1,000 volts per centimeter or more are disclosed in U.S. Pat. No. 4,865,706 and U.S. Pat. No. 4,865,707, as well as pending U.S. patent application Ser. No. 07/359,728 filed May 31, 1989; U.S. patent application Ser. No. 07/406,080 filed Sep. 12, 1989; and U.S. patent application Ser. No. 07/421,609 filed Oct. 13, 1989. These documents are hereby incorporated by reference.

Detector 30 may be any detector having the capability of sensing constituents of the sample as they traverse capillary tube 24, with which the detector communicates. Detectors which operate by sensing change in electromagnetic radiation, such as ultraviolet, infrared, and fluorescence detectors, require that any protective coating of organic material present on capillary tube 24 as supplied must be removed over the area of the capillary on which the detector is to operate.

Another on-column detection principle which may be employed is radioactivity, utilizing an appropriately-designed radioactive sensing device. This detection approach could also be employed with off-line collection and subsequent determination.

It is also possible that the detector employed operates by directly sensing separated sample constituents as they exit capillary tube 24. Examples of such detectors include mass spectrometric detectors and electrochemical detectors. In mass spectrometric detection the exit end 28 of capillary tube 24 is placed in very close proximity to the inlet of a mass spectrometer and an electrode is also placed in close proximity to this capillary end, in contact with the conductive medium exiting the capillary. The field across the capillary is established between this electrode at the capillary's end and the corresponding electrode or wire making contact with the conductive medium in which the capillary tube front end 26 is in contact. In a further alternative detector embodiment, useful where a detector or probe must come into contact with the conductive medium exiting capillary tube 24, the exit end of the capillary tube is connected to a very short additional piece of capillary tube by means of a porous glass sleeve, and this sleeve is immersed in conductive medium. Electrical contacts for the imposition of the electrophoresis field are made with the reservoirs of conductive medium at the respective ends of the capillary tube, and the detector probe is placed in contact with the conductive medium exiting the capillary extension.

The automatic sample handler indicated by dashed box 38 in FIG. 1 may be any of a variety of automatic sample handlers which, operating independently or under control of some external control unit such as a computer, sequentially inject samples onto capillary 24 and position the capillary tube front end 26 in the conductive medium for the running of the electrophoresis.

In operation, waveform generator 12 is configured, manually or by means of instructions from programmable computer 10, to generator the series of voltage pulses desired for the pulsed electric field to be employed in the electrophoresis. The output signal from waveform generator 12 is sent to amplifier 14 where its voltages are raised to the levels desired for the electrophoresis. If the technique of electrophoretic injection is being employed, as illustrated in FIG. 1, the front end 26 of capillary tube 24 is first placed by automatic sample handler 38 into a solution of sample and conductive medium 40 in sample container 42, as shown by the dashed lines in FIG. 1. An electric field, either continuous or pulsed, is then imposed across the capillary for a short time to cause a small amount of sample to migrate into capillary front end 26.

Another injection technique is pressurized injection, in which a small amount of sample solution is forced into the front end of the capillary by application of a positive pressure. Apparatus for this is also known.

Following sample introduction, front end 26 of capillary tube 24 is placed in a container 20 of conductive medium 18, the pulsed field to be employed for the electrophoresis is imposed, and the electrophoresis is carried out according to the protocol previously established.

The series of voltages pulses which result in the pulsed field need not be repetitive, but may be either repetitive or variable and complex. Field pulsing may be applied during selected portions of the electrophoresis run and need not be employed throughout the run. Different combinations of waveforms may be employed during various portions of the electrophoresis run. The times field pulsing is employed can vary in length from one portion of the electrophoresis run to another. In short, the duty cycle of field pulsing can vary with time. Virtually any appropriate combination of pulse shapes, pulse durations, and durations of pulsing in various portions of the electrophoresis run may be employed, to accomplish the desired separations. The particular pulsing conditions best suited for particular separations are experimentally determined.

Automatic sample handler 38, depending on its design, may move the front end 26 of capillary tube 24 between containers 20 and 42, or may hold the front end of the capillary in a fixed position and move containers 20 and 42 so as to bring the capillary into contact with the container contents at appropriate times.

Figure 2:
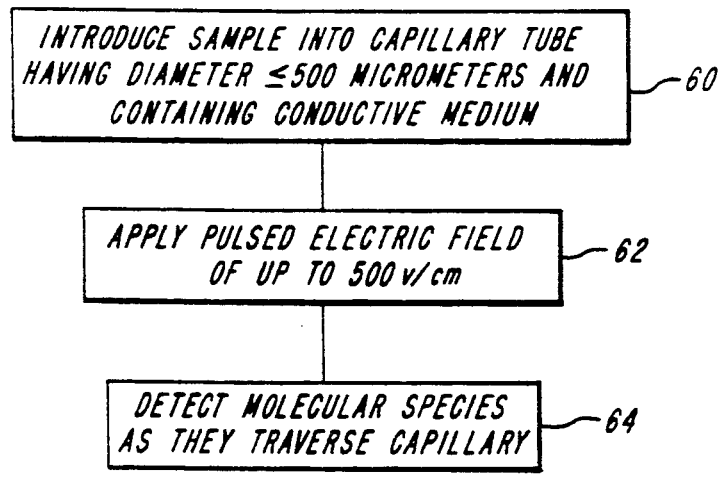
FIG. 2 is a flow chart of the method for conducting pulsed field capillary electrophoresis.

FIG. 2 illustrates the steps of the method for conducting pulsed field capillary electrophoresis. As shown in steps 60, 62, and 64, a sample containing molecular species in a conductive medium is first introduced into a capillary tube having a diameter of less than or equal to 500 micrometers and filled with conductive medium, then subjected to a pulsed electric field amplitude of up to 500 volts per centimeter, and finally, the constituents of the sample are detected as they traverse the capillary.

EXPERIMENTAL

Apparatus

The basic HPCE instrumentation has been described in detail (1). A 60 kV direct current power supply (Model PS/MK60, Glassman Inc., Whitheouse Station, N.J.) was used to generate a potential drop across the capillary for continuous field electrophoresis. For pulsed field experiments a 20 kV operational amplifier (Model PO434, Trek Inc., Medina, N.Y.) controlled with a function generator (Model 185, Wavetek, San Diego, Calif.) was employed. A UV-Vis spectrophotometer (Model 100, SpectraPhysics Inc., San Jose, Calif.) was used at 260 nm to detect the DNA fragments. Column cooling was achieved with air convention by use of a laboratory fan. Each end of the capillary was placed in a buffer reservoir (3 ml) with platinum wire electrodes. In some cases, placing polyacrylamide in the reservoirs was found to be beneficial in extending capillary lifetime. Electrophoresis was performed in fused silica tubing (Polymicro Technologies, Phoenix. Ariz.) of 75 μm i.d. and 375 μm o.d. A detection window was made in the tubing by burning off a 2-4 mm portion of the polyimide coating. The electropherograms were acquired and stored on an IBM PC/XT (Boca Raton. Fla.) via an A/D converter interface (Model 762SB), PE/Nelson, Cupertino, Calif.).

Procedures

Capillary preparation followed procedures described (1, 2). Methacrloxypropyltrimethoxy silane (Petrach Systems, Bristol, Pa.) was first covalently bound to the fused silica capillary walls. Polymerization of polyacrylamide was next accomplished by filling the capillary with degassed, low viscosity arcylamide solution. Polymerization was initiated using APS (ammonium persulfate) and TEMED (N,N,N',N'-tetramethylethylenediamine). Acrylamide solutions were prepared in a buffer of 100 mM Tris base, 100 mM boric acid, 2 mM EDTA, pH 8.3. Samples were injected electrophoretically.

Chemicals

Samples of $\phi$X 174 DNA cut with the restriction enzyme Hae III were obtained from Pharmacia (Piscatawy, N.J.) and New England Biolabs (Beverly, Mass.), and were used at a sample concentration of 500 μg/ml. The solvent for these samples contained 10 mM Tris-HCl (pH 8.0) and 0.1 mM EDTA. The vectors M13mp18 and pBR322, both cut with EcoR I, were obtained from New England Biolabs (Beverly, Mass.). These contained 10 mM Tris-HCl (pH 7.5) and 1 mM EDTA, and were used at a concentration of 100 μg/ml. In addition, pBR322 was dephosphorylated. Ultra-pure Tris base, urea, and EDTA were obtained from Schwartz/Mann Biotech (Cleveland, Ohio). Acrylamide, bis, TEMED and APS were purchased from BioRad (Richmond, Calif.). All buffer and acrylamide solutions were filtered through an 0.2 μm pore size filter (Schleicher and Schuell, Keene, N.H.).

Figure 3A:
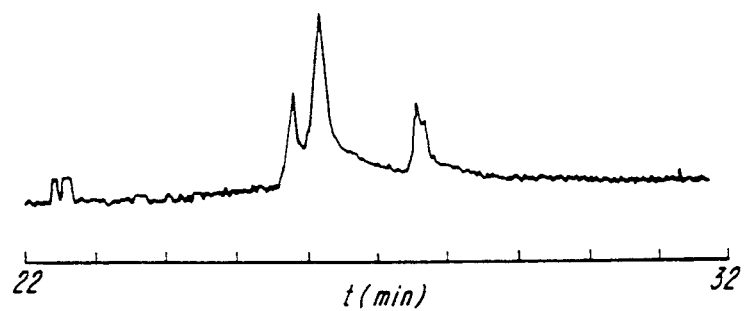
FIG. 3a shows an electropherogram of a Hind III digest of phase lambda on a 12% T linear polyacrylamide capillary column under a constant field of 300 volts per centimeter.
Figure 3B:
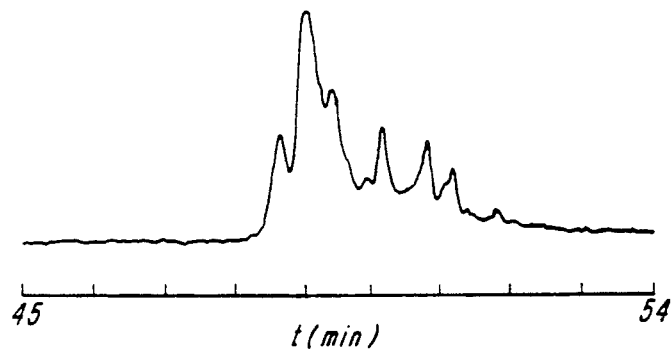
FIG. 3b shows an electropherogram of the same mixture of DNA on the same capillary column as in FIG. 3a, but now run with a pulsed field.

A Hind III digest of phage lambda was subjected to electrophoresis on a 12% linear polyacrylamide-filled capillary (no crosslinking agent) having an internal diameter of 75 micrometers and an effective length of 8 cm, with UV detection at 260 nm. A run conducted under a 300 volts per centimeter continuous field provided the separation shown in FIG. 3a, while an otherwise identical run employing a 0.5 Hz unidirectional square wave field between 0 and 300 volts per centimeter for 15 minutes followed by operation under a 300 volts per centimeter continuous field provided the separation shown in FIG. 3b. In this case the forward pulse with the field on was 3.2 times longer than the time when zero field was applied.

Figure 4:
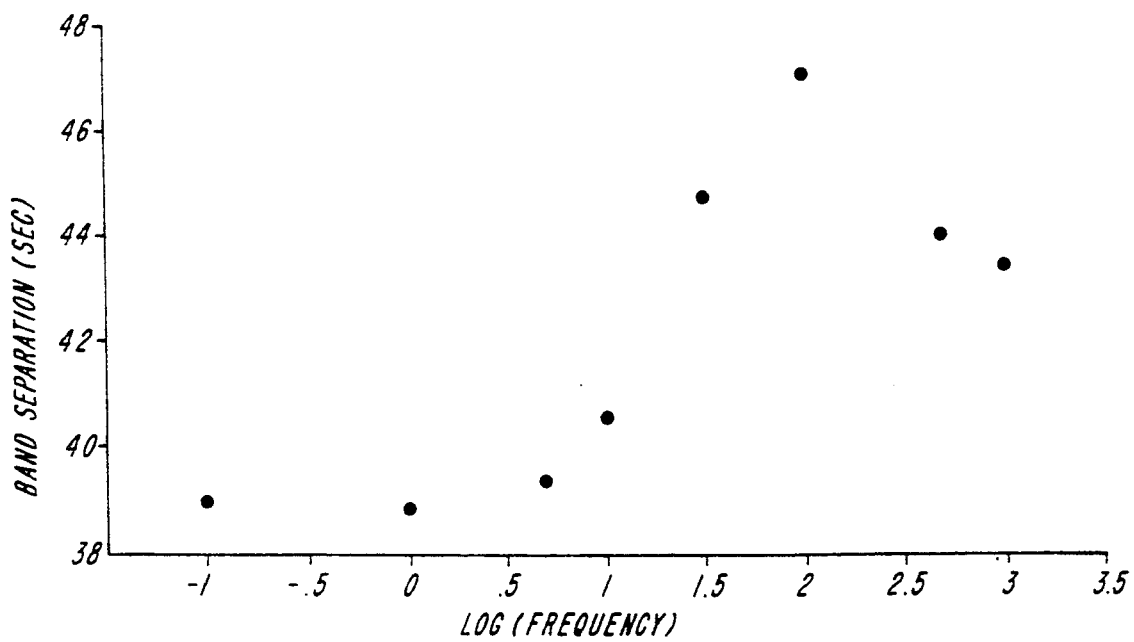
FIG. 4 is a plot of band separation versus log of field pulse frequency for DNA's of 4368 base pairs (bp) and 7250 bp respectively, showing the maximum separation for these materials under the experimental conditions is achieved at a pulse frequency of 100 Hz.

A mixture of EcoRI digests of pBR322 and M13mp18 containing two components of 4363 bp and 7250 bp, respectively, was injected at 7.4 kv for 0.5 seconds and was subjected to pulsed field electrophoresis on a 6% T linear polyacrylamide-filled capillary having an internal diameter of 75 μm and an effective length of 15 cm. Such polymer compositions could not be used in the slab format since it has been noted by others (Chrambach) that at least 10% T is necessary for successful operation. A 100 Hz symmetric square wave filed between 0 and 300 volts per centimeter was employed. Relative to electrophoresis on the same capillary with continuous field operation at 300 volts per centimeter, the pulsed field run provided a 20% increase in peak separation. This frequency was determined to be the optimum for this pair of DNA molecules, as seen in FIG. 4, which is a plot of band separation vs log of pulsed frequency.

Figure 5B:
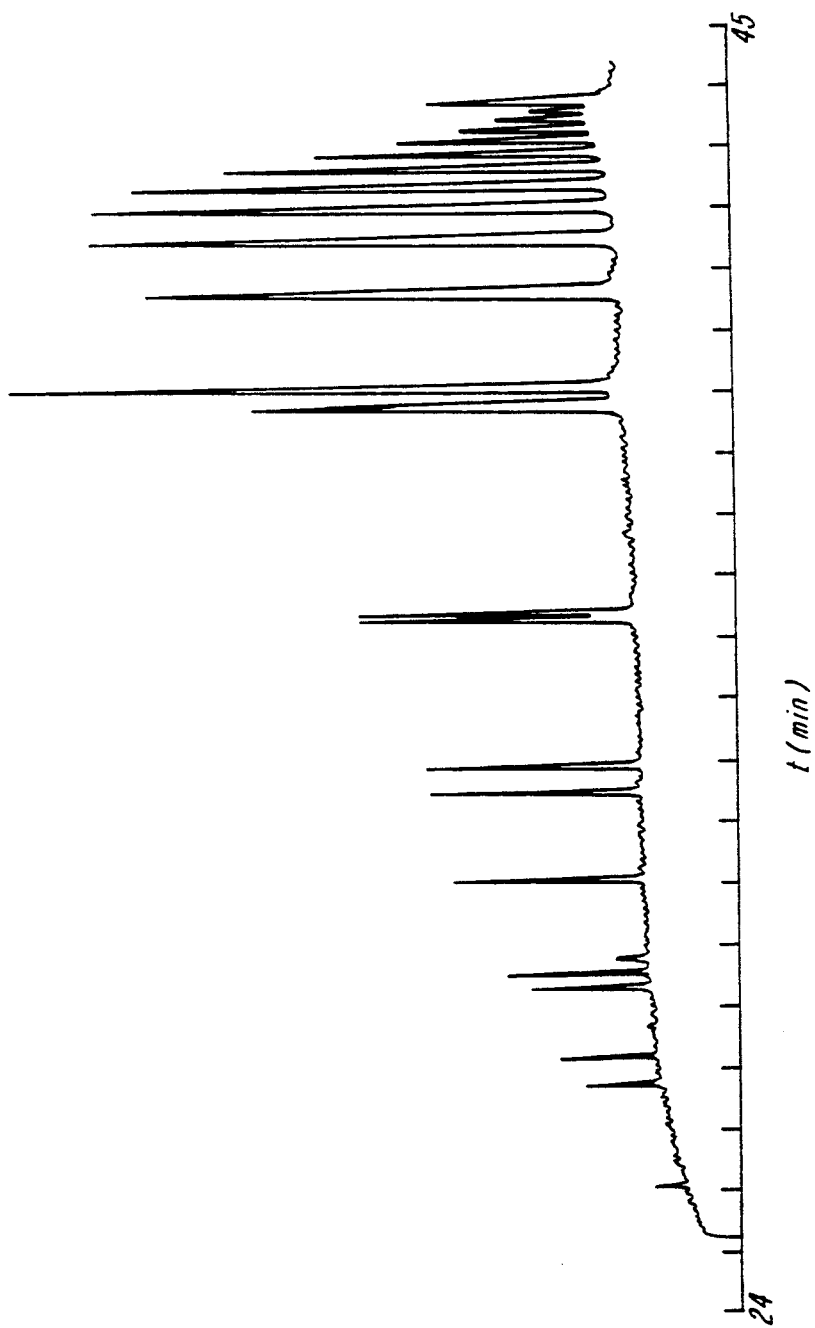
FIG. 5b is an electropherogram showing the separation of the 1 kb ladder of DNA molecules of FIG. 5a on the same column, but with filed pulsing being employed at the start of the run.

FIGS. 5a and 5b show another example of pulse field electrophoresis in the separation of a 1 kb ladder which is a mixture of DNA molecules from 75 bp to 12,000 bp. FIG. 5a shows the separation in continuous field at 250 volts per centimeter. FIG. 5b shows asymmetric field inversion electrophoresis in which the square waves had a positive amplitude of 250 V/cm followed by a negative amplitude of 36 V/cm. The forward pulse was applied for 3 times longer than the reverse field. The pulsed waveform at 10 Hz was run for 25 min, followed by a continuous field of 250 V/cm. Separation is improved by pulsing as evidenced by the enhanced resolution of components 506 and 516 bp. See expanded scale in FIGS. 5c and 5d. It is again noted that the column, 4% T, 0% C, is well below that possible for slab gel operation.

FIGS. 6a and 6b show the separation of φX174 digested with enzyme Hae III on a 9% T, 0% C polyacrylamide capillary. This sample contains species ranging from 75 bp to 1358 bp. FIG. 6a was run at a continuous field of 285 V/cm. FIG. 6b was run using a pulsed field consisting of an asymmetric triangle wave. The forward pulse, to 285 V/cm, had a rise time of 45 seconds and the reverse pulse, to 14 V/cm, had a fall time of 10 seconds. This waveform was repeated at 0.02 Hz for 24 minutes, after which, a continuous field of 285 V/cm was applied. The separation in time units of species 1 and 11 was improved 16% by field pulsing. The separation of species 8 and 11 was similarly improved 33%.

REFERENCES

1. B. L. Karger, et al., J. Chromatog., 458, 303 (1988).
2. A. Guttman, et al., Anal. Chem., 62, 137 (1990).

Other embodiments of the invention will be apparent to those skilled in the art from a consideration of this specification or practice of the invention disclosed herein. It is intended that the specification and examples be considered as exemplary only, with the true scope and spirit of the invention being indicated by the following claims.

We claim:

1. Apparatus for separating and detecting a plurality of molecular species of a sample in conductive medium, comprising:
   a capillary tube containing a conductive medium including a sieving matrix, said tube having a cross-sectional dimension of not more than 500 micrometers;
   means for introducing said sample into said conductive medium-filled capillary tube;
   means for applying a pulsed electric field across said conductive medium-filled capillary tube, between the ends thereof; said pulsed electric field enhancing the separation of said plurality of molecular species of said sample as said sample migrates through said sieving matrix contained within said capillary tube; and
   means for detecting said plurality of molecular species of said sample as said plurality of molecular species migrate within said capillary tube.

2. The apparatus of claim 1, wherein said sieving matrix comprises a polymeric material.

3. The apparatus of claim 2, wherein said polymeric material is crosslinked.

4. The apparatus of claim 1, wherein said means for introducing a sample into a capillary tube comprises an automatic sample handling device.

5. The apparatus of claim 1, wherein said means for applying a pulsed electric field comprises a waveform generator.

6. The apparatus of claim 5, wherein said means for applying a pulsed electric field further comprises an amplifier, the input of said amplifier being electrically connected to the output of said waveform generator, and the output of said amplifier being electrically connected to the respective ends of said capillary tube.

7. The apparatus of claim 6, wherein said means for applying a pulsed electric field further comprises a programmable computer having a communication port which is connected to the input of said arbitrary waveform generator.

8. The apparatus of claim 1, wherein said means for detecting comprises a detector in communication with a translucent section of said capillary tube, said detector being sensitive to change in electromagnetic radiation resulting from transit of constituent molecular species of said sample through said capillary tube.

9. The apparatus of claim 1, wherein said means for detecting comprises a mass spectrometer.

10. The apparatus of claim 1, wherein said means for detecting comprises an electrochemical detector.

11. The apparatus of claim 1, wherein said means for detecting comprises a radioactivity-sensing detector.

12. A method for separating and detecting a plurality of molecular species of a sample in conductive medium, comprising:
   introducing said sample into a capillary tube having a cross-sectional dimension of not more than 500 micrometers, and filled with conductive medium including a sieving matrix;
   applying a pulsed electric field of up to 500 volts per centimeter across said capillary tube, between the ends thereof; said pulsed electric field enhancing the separation of said plurality of molecular species of said sample as said sample migrates through said sieving matrix contained within said capillary tube; and
   detecting said plurality of molecular species of said sample as said plurality of molecular species migrate within said capillary tube.

13. The apparatus of claim 12, wherein the sample is introduced into the capillary tube by electrophoretic injection.

14. The apparatus of claim 12, wherein the sample is introduced by pressurized injection.

15. The apparatus of claim 12, wherein in the step of applying a pulsed electric field, the pulses are unidirectional relative to a zero field state.

16. The apparatus of claim 12, wherein in the step of applying a pulsed electric field, the applied field is positive.

17. The apparatus of claim 12, wherein in the step of applying a pulsed electric field, the pulses are bidirectional relative to a zero field state.

18. The apparatus of claim 12, wherein in the step of applying a pulsed electric field, the frequency of the pulses varies with time.

19. The apparatus of claim 12, wherein in the step of applying a pulsed electric field, the waveform of the pulses varies with time.

20. The apparatus of claim 12, wherein in the step of applying a pulsed electric field, the amplitude of successive pulses varies with time.

21. The apparatus of claim 12, wherein in the step of applying a pulsed electric field, the duty cycles varies with time.

22. The apparatus of claim 12, wherein the capillary tube includes polymeric material at a level less than 10% T.

* * * * *

UNITED STATES PATENT AND TRADEMARK OFFICE
CERTIFICATE OF CORRECTION

PATENT NO. : 5,122,248

DATED : June 16, 1992

INVENTOR(S) : Karger et al.

It is certified that error appears in the above-identified patent and that said Letters Patent is hereby corrected as shown below:

Column 1, line 12, "is allow" should read --is a low--.

Signed and Sealed this

Fifth Day of April, 1994

Attest:

BRUCE LEHMAN

Attesting Officer

Commissioner of Patents and Trademarks